United States Patent
Bruder et al.

(10) Patent No.: US 6,937,690 B2
(45) Date of Patent: Aug. 30, 2005

(54) METHOD FOR COMPUTED TOMOGRAPHY OF A PERIODICALLY MOVING OBJECT TO BE EXAMINED, AND A CT UNIT FOR CARRYING OUT THIS METHOD

(75) Inventors: Herbert Bruder, Hoechstadt (DE); Thomas Flohr, Uehlfeld (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1 day.

(21) Appl. No.: 10/700,677

(22) Filed: Nov. 5, 2003

(65) Prior Publication Data

US 2004/0131140 A1 Jul. 8, 2004

(30) Foreign Application Priority Data

Nov. 5, 2002 (DE) .......................................... 102 51 448

(51) Int. Cl.[7] .............................................. A61B 6/03
(52) U.S. Cl. .............................. 378/15; 378/8; 378/901
(58) Field of Search .......................... 378/4, 8, 15, 19, 378/901

(56) References Cited

U.S. PATENT DOCUMENTS

| 6,266,553 | B1 | 7/2001 | Fluhrer et al. |
| 6,408,043 | B1 | 6/2002 | Hu et al. |
| 6,556,697 | B1 | 4/2003 | Bruder et al. |
| 2003/0068015 | A1 | 4/2003 | Bruder et al. |
| 2003/0072419 | A1 | 4/2003 | Bruder et al. |
| 2004/0179644 | A1 * | 9/2004 | Tsuyuki .......................... 378/8 |

\* cited by examiner

*Primary Examiner*—David V Bruce
(74) *Attorney, Agent, or Firm*—Harness, Dickey & Pierce, P.L.C.

(57) ABSTRACT

A method is for producing CT images of a periodically moving object to be examined, in particular a method for cardio volume reconstruction for multi-row CT units in spiral mode. A multi-row CT unit designed is further designed therefore. A small partial revolution segments along a revolution spiral is used to calculate in each case per partial revolution segment a plurality of segment images that are converted in a second step to partial images in the target image plane (for example axial plane) and are assembled with the correct phase to form complete images.

44 Claims, 5 Drawing Sheets

METHOD FOR COMPUTED TOMOGRAPHY OF A PERIODICALLY MOVING OBJECT TO BE EXAMINED, AND A CT UNIT FOR CARRYING OUT THIS METHOD

The present application hereby claims priority under 35 U.S.C. §119 on German patent application number DE 102 51 448.8 filed Nov. 5, 2002, the entire contents of which are hereby incorporated herein by reference.

FIELD OF THE INVENTION

The invention generally relates to a method for computed tomography. Preferably, it is for the purpose of examining a periodically moving object to be examined, in particular to a cardio computed tomography method. It is also generally related to a computed tomography unit for carrying out this method.

The scanning of the area to be examined may be carried out by a detector array of planar design, while the detector array is moving in a fashion rotating about the system axis on a spiral path, and absorption data are collected. At the same time, movement data are collected by the periodically moving area to be examined, in order to be able to assign the detector data and data resulting therefrom to the movement states, only output data that are correlated with a specific movement state of the body region being used to compose a CT image or a set of CT images.

BACKGROUND OF THE INVENTION

A method and a CT unit are disclosed, for example, in the closest DE 198 42 238 A1. This application discloses an image reconstruction recording method for a periodically moving object with the aid of a movement phase and a rest phase by means of a detector unit that is arranged on a gantry and has at least a first and a last detector row, in which:

the first and the last detector row run perpendicular to an axis of rotation and are spaced apart from one another parallel to the axis of rotation by a detector height (D), the object is displaced along the axis of rotation relative to the gantry at a feed rate, and the gantry is rotated about the axis of rotation at a rotational speed, at least during the rest phases, per angle of rotation from a group of angles of rotation the detector rows respectively simultaneously record one measured data record each that is assigned to the respective angle of rotation, the rotational speed is selected in such a way that during a rest phase, the gantry rotates through a rotation angle that is at least as large as a reconstruction angular range required to reconstruct the object, the feed rate is selected in such a way that the object is displaced along the axis of rotation by at most the detector height during the sum of a movement phase and two reconstruction times, and the reconstruction time is the time required to sweep over the reconstruction angular range.

A disadvantage of this method and CT unit is that no cone-beam correction is provided and that, therefore, as the cone angle becomes larger, image artifacts are produced that exert a negative influence on the image quality.

Just as in accordance with the publications DE 198 42 240 A1, DE 197 40 214 A1 and DE 100 63 636 A1, in this method a reconstruction method is applied that requires a reconstruction of data records that provide overall a complete CT image.

Reference is also made to German laid-open patent application DE 102 07 623 A1, which is not a prior publication.

This application discloses a method for cardio computed tomography and a cardio computed tomography device in which, for the purpose of scanning an object with the aid of a conical beam emanating from a focus and of a matrix-type detector array for detecting the beam, the focus is moved relative to the object on a spiral path whose central axis corresponds to a system axis, the detector array supplying output data corresponding to the received radiation. Further, for the purpose of imaging an object area executing a periodic movement, a signal reproducing the temporal variation in the periodic movement being obtained during the scanning and images with an inclined image plane being reconstructed from output data respectively supplied during the movement of the focus on a spiral segment. The image planes is inclined with reference to the system axis both by an angle of inclination about a first axis cutting the system axis at right angles, and by a tilt angle about a second axis cutting both the first axis and the system axis at right angles, directly consecutive spiral segments overlapping one another by an overlap angle that is greater than or equal to zero. Finally, the spiral segments are selected taking account of the signal reproducing the temporal variation in the periodic movement such that they correspond to a phase of the periodic movement that is to be imaged.

Although the conical course of the beam between the focus and multi-row detector is taken into account in the method indicated there, the sector data of a plurality of neighboring similar movement cycles being taken into account for constructing the image, the temporal resolution cannot be increased independently of heart rate.

Furthermore, German laid-open patent application DE 101 33 237 A1, which is not a prior publication, sets forth a method for computed tomography and a CT unit in which:

for the purpose of scanning an object with the aid of a conical beam emanating from a focus and of a matrix-type detector array for detecting the beam, the focus is moved relative to the object on a spiral path about a system axis, the detector array supplying output data corresponding to the received radiation, and the output data respectively supplied during the movement of the focus on the spiral path being divided into output data with reference to subsegments, segment images with an image surface inclined with reference to the system axis being reconstructed for the subsegments, a signal reproducing the temporal variation in a periodic movement being obtained during the scanning in order to image an object area executing the periodic movement, the segment images being assigned a z position on the system axis and a temporal position with reference to the temporal variation in the periodic movement, segment images belonging to a desired range of z positions and a desired range of temporal positions being selected in such a way that the corresponding subsegments have a total length sufficient to reconstruct a CT image, and the selected segment images being combined at least indirectly to form a resulting CT image with reference to a target image surface.

This method also takes account of the conical course of the ray, but the temporal resolution can be controlled only if the table feed is selected to be suitably small during data acquisition.

Finally, reference is made to German laid-open patent application DE 101 27 269 A1, which is likewise not a prior publication and which discloses a method and unit for computed tomography in the case of which, in order to scan an unmoving object with the aid of a conical beam emanating from a focus and of a matrix-type detector array for detecting the beam, the focus is moved relative to the object on a spiral path about a system axis. The detector array supplies output data corresponding to the received radiation. The output data respectively supplied during the movement of the focus on a spiral segment with a length sufficient to reconstruct a CT image is divided into output data with reference to subsegments. Segment images with an image plane inclined with reference to the system axis are reconstructed for the subsegments. The segment images respectively belong to a subsegment being combined to form a component image with reference to a target image plane. Finally, the component images are combined to form a resulting CT image with reference to the target image plane.

SUMMARY OF THE INVENTION

It is the object of an embodiment of the invention to make available a method for computed tomography for examining a periodically moving object to be examined. In particular, an embodiment of the invention relates to a cardio computed tomography method, and a computed tomography unit for carrying out this method. On the one hand, an aim may be to take the cone angle into account. On another hand, optimal utilization of the detector, and thus of the dose, may be provided even in the case of variable feed values or pitches of the movement spiral of the detector below a maximum feed value.

The inventor has discovered that a method of segmented spiral reconstruction with the aid of multi-row CT that is set forth in principle in the above-named laid-open patent application DE 101 27 269 A1, the entire contents of which are incorporated herein by reference, could also be used for examining a cyclically moving object such as a heart, for example, by adding suitable axial segment image planes with the correct phase.

On the basis of this method for image reconstruction, the inventors now propose that, after the reconstruction and reformatting of volume stacks of axial segment image planes, the stacks be marked with a temporal position and z position and subsequently superimposed by a spatial and time filter with reference to the cyclic movement of the object to be examined, such that images of specific and identical movement situations are respectively produced.

In the case of a heart to be examined as the cyclically moving object to be examined, for example, the temporal position can be yielded from the ECG of the patient recorded simultaneously with the measurement. It is then necessary for the purpose of retrospective gating to determine suitable segments that complement one another to form an angular range of $\pi$, and to sum corresponding axial segment image planes to form the target image.

Thus, according to an embodiment of the invention, there is defined on the set of the segment image planes $S(\theta_{R,j}+k\pi, Z_{R,q}(\theta_{R,j}+k\pi); 1 \leq j \leq N_{seg}/2$ (whole numbers k,q) a spatio-temporal filter function by means of which the z resolution and temporal resolution of the target image can be influenced over a wide range.

In this case, $\theta_{R,j}+k\pi$ denotes the central angle of the jth volume stack in the kth half revolution ($\theta_{R,j}=\theta_R+(j-1)\cdot\pi/(N_{seg}/2)$), and $$z_{R,q}(\theta_{R,j}+k\pi) = z_{start}(\theta=0) + p\cdot\frac{\theta_{R,j}+k\pi}{2\pi} + (q - N_{tilt}/2)\cdot\Delta z$$

denotes the assigned z positions of the segment image planes in the volume stack, p being the table feed and $z_{start}$ being the starting position of the spiral revolution at the projection angle $\theta=0$. Otherwise, the segment image planes are functions of the spatial coordinates (x,y), which have initially been omitted for the sake of clarity.

The filtered segment image plane $\hat{S}(\theta_{R,j}, z_{img})$ relating to the central angle $\theta_{R,j}$ at the z position $z_{img}$ is calculated as follows:

$$\hat{S}(\theta_{R,j}, z_{img}) = \frac{1}{W_j}\cdot\sum_{k,q}S(\theta_{R,j}+k\pi, z_{R,q}(\theta_{R,j}+k\pi))\cdot w_z(d(z_{R,q}(\theta_{R,j}+k\pi)z_{img}))\cdot$$

$$w_{phase}(t(\theta_{R,j}+k\pi)-c_R(k)); \text{ where } 1 \leq j \leq N_{seg}/2,$$

$w_z$ being a suitable weighting function that determines the layer thickness, and d denoting the distance or a similar function of the segment image plane at the z position $z_{R,q}$ from the z position $z_{img}$.

$$W_j = \sum_{k,q}w_z(d(z_q(\theta_{R,j}+k\pi, z_{img}))\cdot w_{phase}(t(\theta_{R,j}+k\pi)-c_R(k,j))$$

is the weighted sum for correct normalization. The weighting function $w_{phase}$ evaluates the temporal spacing of the segment image planes centered at the angle $\theta_{R,j}+k\pi$ from the temporal position $c_R(k,j)$ determined by means of the ECG in the cardiac cycle assigned to the angle $\theta_{R,j}+k\pi$.

The CT image at the z position $z_{img}$ is then yielded in accordance with:

$$I(x, y, z_{img}) = \frac{1}{N_{seg}/2}\cdot\sum_{j=1}^{N_{seg}/2}\hat{S}(\theta_{R,j}, x, y, z_{img}).$$

Both the temporal resolution and the z resolution of the target images can be influenced over a wide range by suitable selection of the table feed and of the weighting function. This is helpful, in particular, for functional cardiac examinations, which require pictures during the contraction phase of the heart, and thus a high temporal resolution. On the other hand, a high z sharpness is necessary for the 3D illustration of the coronary anatomy in coronary angiography. Consequently, a narrow z filter is to be selected, and the temporal resolution can be selected only in a restricted range for a given table feed. In the unfavorable case with a large feed and a high desired z sharpness, the segment images required to calculate the target image must be taken from only one cardiac cycle. Consequently, in this case the achievable temporal resolution is limited to half the rotational time of the scanner.

The aim below is to describe the basic image reconstruction method without taking account of the cyclic movement of the object to be examined. However, it is to be borne in mind that, in the case of the method according to the invention, at least the segment images are also provided with a kind of time stamp that respectively permits a correlation to be made with the phase of the cyclic movement of the object to be examined.

In this image reconstruction method, an object is scanned spirally in segments and the data of a spiral segment are divided into subsegments, and segment images are reconstructed with reference to these subsegments. In this case, the deviations of the image planes of the segment images from the spiral path are very small along the subsegments, and so the segment images contain only very small errors caused by deviations of the image planes of the segment images from the spiral path along the subsegments. Thus the image quality to be expected upon the production of the resulting CT image is high.

The maximum inclination of the image planes of the segment images is determined from the condition that rays for the image plane of the respective segment image must be present at both ends of a subsegment within the measuring field.

The segment images, which cannot be used on their own, are calculated in a way known per se, that is to say the projections, present in parallel or fan-beam geometry, for the respective subsegment are used to select, in accordance with a suitable error criterion, the rays that are most favorable for the image plane of the respective segment image, and to filter them and back-project them or reconstruct them with the aid of another standard method.

The combination of the segment images belonging to a subsegment, that is to say their reformatting to form a target image plane, leads to a component image that can likewise not be used on its own; only once the component images of all the component images belonging to the respective spiral segment have been combined, with reference to the desired target image plane, to form a resulting CT image is a useful image produced.

The image quality thereof is particularly high whenever the segment images are reconstructed for image planes that are inclined with reference to the system axis both by an angle of inclination $\gamma$ about a first axis cutting the system axis at right angles, and by a tilt angle $\delta$ about a second axis cutting both the first axis and the system axis at right angles, because then the adaptation of the image planes of the segment images to the spiral path of the respective subsegment is further improved.

When the mutually neighboring subsegments overlap, the output data belonging to the overlap regions should be weighted in such a way that the weights of mutually corresponding output data of the subsegments overlapping one another yield one in each case.

The advantage of overlapping subsegments resides in the fact that artifacts that can otherwise occur at the joints between the subsegments are avoided.

Furthermore, segment images for a number $n_{ima}$ of inclined image planes can be reconstructed for each subsegment, the image planes having different z positions $z_{ima}$. Through the reconstruction of a plurality of segment images with a differently inclined image plane for different z positions, it is possible by appropriately selecting the angle of inclination $\gamma$ and the tilt angle $\delta$ to adapt the image plane of the respective segment image optimally to the subsegment for each of these z positions, and to use both the detector array and the dose completely, in theory, and to the greatest possible extent in practice. In this case, the plurality of inclined image planes may intersect in a straight line running tangential to the subsegment.

In order to obtain the fullest possible utilization of detector and dose, in accordance with a variant of the invention, it holds for the extreme values $+\delta_{max}$ and $-\delta_{max}$ of the tilt angle $\delta$ of the inclined image planes belonging to a subsegment that:

$$\pm\delta_{max} = \arctan\left(\frac{-\frac{SM}{2} + Sp\frac{\alpha_l}{2\pi} \pm RFOV\cos\alpha_l \tan\gamma_0}{-\frac{R_f}{\cos\gamma_0} - (\pm RFOV)\frac{\sin\alpha_l}{\cos\gamma_0}}\right)$$

$\gamma_0$ being the value of the angle of inclination $\gamma$ determined for the tilt angle $\delta=0$ in accordance with $$\gamma_0 = \arctan\left(\frac{-Sp\,\hat{\alpha}}{2\pi R_f \sin\hat{\alpha}}\right).$$

In the interest of a high image quality, in accordance with a further variant of an embodiment of the invention, it is provided that, for a given absolute value $|\delta_{max}|$ of the maximum value of the tilt angle $\delta$, the associated optimal value $\gamma_{min}$ of the angle of inclination $\gamma$ is determined in such a way that an error criterion, for example the minimum quadratic mean of the distance, measured in the z direction, of all the points of the subsegment from the image plane, is fulfilled.

In order to create the precondition for being able to obtain the transaxial tomographic images to which the users of CT units are accustomed, it is advantageously possible to provide reformatting, a component image being produced in a further method step by combining a plurality of segment images. In this case, the combination can be performed by combining a plurality of segment images to form a component image by interpolation or, in particular, by weighted averaging.

The reconstruction layer thickness of the component images, and thus of the resulting CT image is set according to a particularly preferred embodiment of the invention by virtue of the fact that, when being combined to form a component image, the segment images are weighted in accordance with the respectively desired reconstruction layer thickness of the component image.

When a plurality of segment images are combined to form a component image, it is possible for the number of the segment images that are combined to produce a component image to be selected in accordance with the respectively desired reconstruction layer thickness of the component image. In this case, it is possible in the interest of the highest possible image quality to reconstruct the segment images with the smallest possible layer thickness.

The combination of the component images to form the resulting CT image is preferably performed by adding and, specifically, likewise preferably for a target image plane that cuts the system axis at right angles. The target image plane can, however, also be inclined with reference to the system axis.

In order to keep within bounds the quantity of data occurring during the production of segment images, one variant of the invention provides that the data corresponding to the segment images are compressed.

In accordance with a particularly preferred embodiment of the image reconstruction, it can be provided that the compressed data corresponding to the segment images have a pixel matrix which is inhomogeneous in such a way that the resolution in a first direction running at least substantially in the direction of the reference projection direction belonging to the respective subsegment is higher than in a second direction which runs at least substantially orthogonal to the reference projection direction. Such a procedure is possible because the information density in the segment images orthogonal to the reference projection direction belonging to the respective subsegment is substantially higher than in the reference projection direction belonging to the respective subsegment.

The implementation of an inhomogeneous pixel matrix is particularly simple in the case when the compressed data corresponding to the segment images have pixels of elongated shape, preferably rectangular pixels, the longest extension of the pixels running at least substantially in the direction of the reference projection direction belonging to the respective subsegment.

It is particularly time saving when, in accordance with a further preferred embodiment of the invention, the segment images are reconstructed in the inhomogeneous pixel matrix, since then substantially fewer pixels need to be reconstructed than in the case of a homogeneous pixel matrix that has the same resolution in the reference projection direction belonging to the respective subsegment. The back projection is of particularly simple configuration when the back projection direction corresponds at least substantially to the direction of the reference project direction belonging to the respective subsegment.

Since the resulting CT image usually has a homogeneous pixel matrix, in accordance with one variant of an embodiment of the invention, if the compression is based on the use of an inhomogeneous pixel matrix, it is to be canceled at the latest in the course of the combination of the component images to form the resulting CT image.

In particular variants of the image reconstruction method, the pixels of the homogeneous pixel matrix can be obtained by interpolation or by averaging from the pixels of the inhomogeneous pixel matrix.

It may be pointed out that the described method can be carried out without a cone correction. In this case, the spiral is decomposed into $N_{seg}$ small (for example, $\pi/4$, $\pi/8$, ...), if appropriate slightly overlapping, partial revolution segments. Axial segment image planes are defined at the spacing $\Delta z$ for each of these segments and reconstructed to form axial image layers $S(\theta_{R,j}+k\pi, Z_{R,q} (\theta_{R,j}+k\pi))$; $1 \leq j \leq N_{seg}/2$ (whole numbers k, q). These can then be calculated again to form target images at freely selectable z positions with a selectable time resolution.

On the basis of the above-described method, the inventors also propose a CT unit having at least one beam emanating from a focus and having a detector array of planar design with a multiplicity of distributed detector elements for detecting the rays of the beam. The at least one focus may be moved relative to the object to be examined on at least one focal path, running around the object to be examined, with a detector array situated opposite. At least a device for detecting the movement state of the object to be examined may be included, for collecting detector data, and for filtering and back projection being provided in accordance with the above-described method.

The functional device required in this method according to an embodiment of the invention can be implemented at least partially by programs or program modules. Furthermore, an ECG can be used to detect the movement state if a patient's heart is concerned in this case. However, it is also possible in the case, for example, of an examination of a periodically moving machine to use an angle sensor or some other measuring instrument from which the phase respectively present or the current movement state can be detected.

BRIEF DESCRIPTION OF THE DRAWINGS

The present invention will become more fully understood from the detailed description of preferred embodiments given hereinbelow and the accompanying drawings, which are given by way of illustration only and thus are not limitative of the present invention, and wherein.

DETAILED DESCRIPTION OF THE PREFERRED EMBODIMENTS

Figure 1:
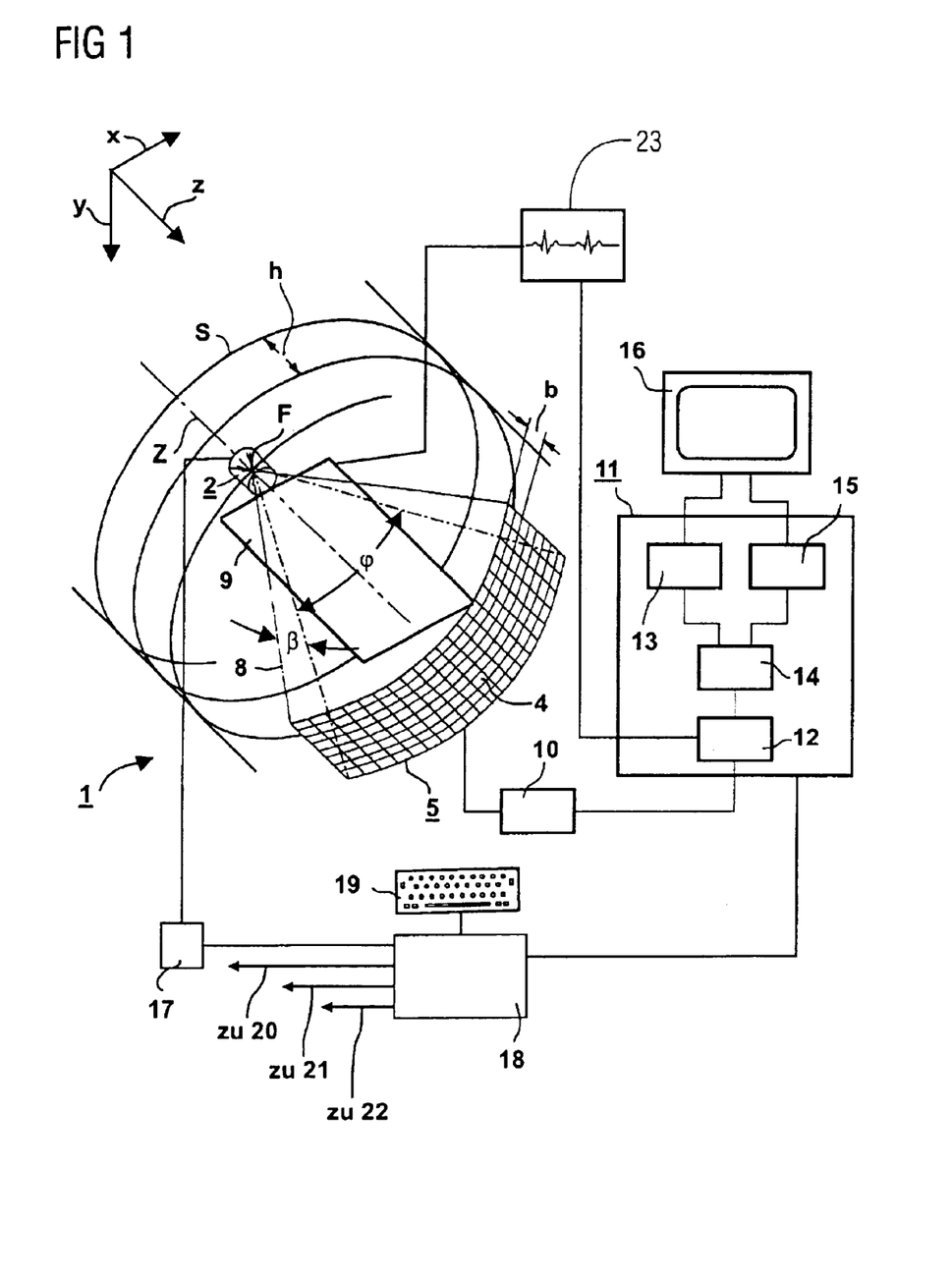
FIG. 1 shows a schematic illustration of a multi-row CT unit.
Figure 2:
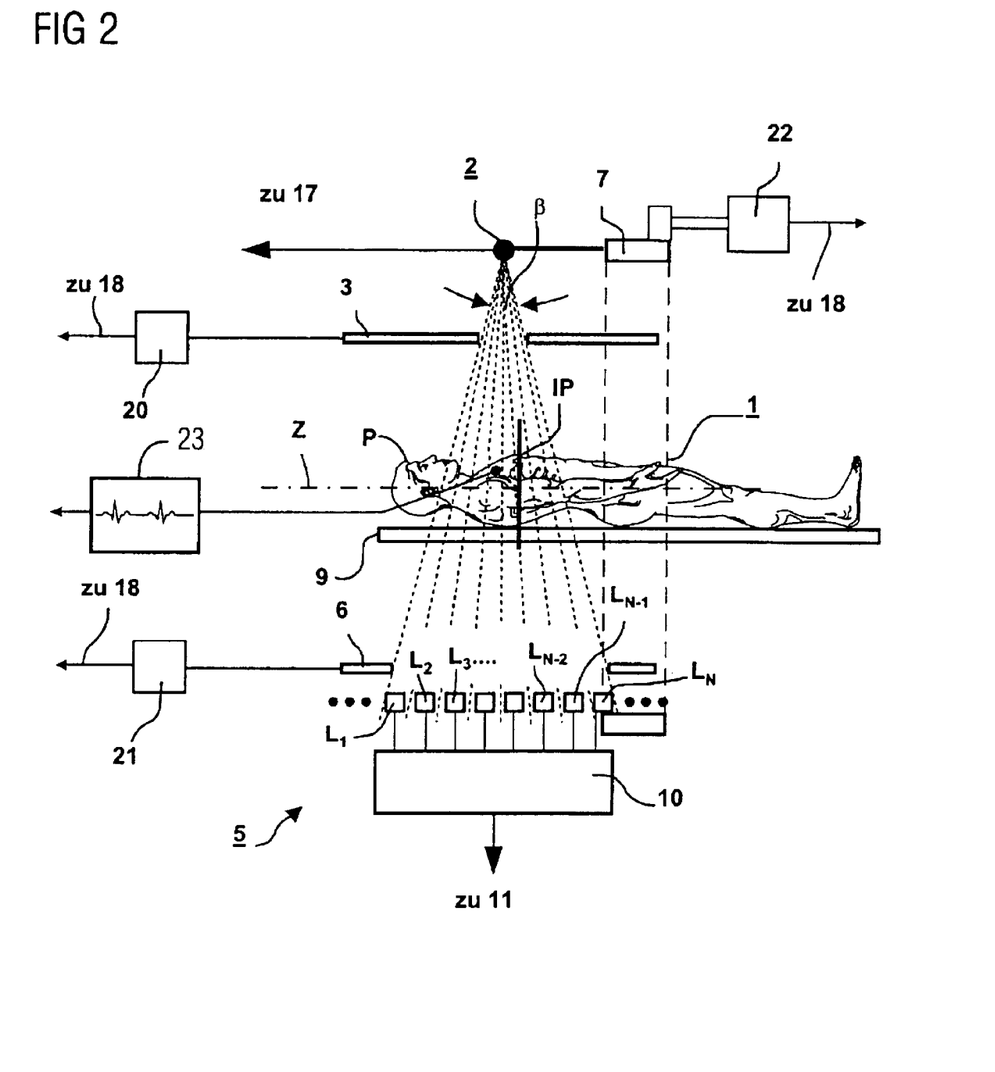
FIG. 2 shows a longitudinal section through the unit from FIG. 1.

The two FIGS. 1 and 2 show a CT unit of the third generation which is suitable for carrying out the method according to an embodiment of the invention. Its overall measuring arrangement 1 has an X-ray source 2 with a radiation aperture 3 placed in front of it and close to the source, and a detector system 5, constructed as a two-dimensional array of a plurality of rows and columns of detector elements 4 and with a radiation aperture 6 placed in front of it and close to the detector. In FIG. 1, for reasons of clarity, only eight rows of detector elements 4 are illustrated, but the detector system 5 has further rows of detector elements 4, which is indicated by dots in FIG. 2.

The X-ray source 2 with the radiation aperture 3, on the one hand, and the detector system 5 with the radiation aperture 6, on the other hand, are arranged opposite each other on a rotary frame 7 in such a way that a pyramidal X-ray beam which, during the operation of the CT unit, originates from the X-ray source 2 and is collimated by the adjustable radiation aperture 3 and whose edge rays are designated by 8, strikes the detector system 5. In the process, the radiation aperture 6 is set to correspond to the cross section, set by way of the radiation aperture 3, of the X-ray beam in such a way that only that area of the detector system 5 which can be struck directly by the X-ray beam is exposed. In the operating mode illustrated in FIGS. 1 and 2, this is eight rows of detector elements 4, which are referred to as active rows below. The further rows indicated by dots are covered by the radiation aperture 6 and are therefore inactive. Each row of detector elements 4 has a number K of detector elements, k=1 to K being the so-called channel index. The active rows $L_n$ of detector elements 4 are designated by $L_1$ to $L_N$ in FIG. 2, n=1 to N being the row index.

The X-ray beam has the cone angle $\beta$, plotted in FIG. 2, which is the opening angle of the X-ray beam in a plane containing the system axis Z and the focus F. The fan angle $\phi$ of the X-ray beam, which is the opening angle of the X-ray beam in a plane lying at right angles to the system axis Z and containing the focus F, is plotted in FIGS. 1 and 2.

The rotary frame 7 can be set rotating about a system axis designated by Z by means of a drive device 22. The system axis Z runs parallel to the z axis of a three-dimensional rectangular coordinate system illustrated in FIG. 1.

The columns of the detector system 5 likewise run in the direction of the z axis, while the rows, whose width b is measured in the direction of the z axis and is 1 mm, for example, run transversely with respect to the system axis Z and the z axis.

In order to be able to bring a moving object to be examined, for example a patient's P heart, into the beam path of the X-ray beam, a bearing device 9 is provided, which can be displaced parallel to the system axis Z, that is to say in the direction of the z axis, specifically in such a way that there is synchronization between the rotational movement of the rotary frame 7 and the translational movement of the bearing device, with the effect that the ratio between translational and rotational speeds is constant, it being possible to adjust this ratio by a desired value for the feed p of the bearing device being selected per rotation of the rotary frame.

It is therefore possible for a volume of an object to be examined, which is located on the bearing device 9, to be examined in the course of volume scanning. It is possible for the volume scanning to be performed in the form of spiral scanning with the effect that, with simultaneous rotation of the measuring unit 1 and translation of the bearing device 9, a large number of projections from various projection directions is recorded by way of the measuring unit per revolution of the measuring unit 1. During the spiral scanning, the focus F of the X-ray source is moved relative to the bearing device 9 on a spiral path S.

At the same time as the scanning of the object to be examined, the cardiac activity of the patient is recorded by an ECG 23 in order to be able later to weight the determined image data with the correct phase in accordance with the ECG pictures.

The measured data read out in parallel from the detector elements of each active row of the detector system 5 during the spiral scanning and corresponding to the individual projections are subjected to digital/analog conversion in a data conditioning unit 10, are serialized and transmitted to an image computer 11.

After the measured data have been preprocessed in a preprocessing unit 12 belonging to the image computer 11, the resulting data stream passes to a reconstruction unit 13, which uses the measured data to reconstruct CT images of desired layers of the object to be examined, and specifically using a method known per se (for example 180LI or 360LI interpolation).

The CT images include pixels assembled in the form of a matrix, the pixels being associated with the respective image plane. Each pixel is assigned a CT number in Hounsfield units (HU). The individual pixels are displayed in accordance with a CT index/gray value scale with a gray value corresponding to their respective CT number.

The images reconstructed by the slice reconstruction unit 13 and the shadowgram reconstruction unit 15 are displayed on a display unit 16, for example a monitor, connected to the image computer 11.

The X-ray source 2, for example an X-ray tube, is supplied by a generator unit 17 with the requisite voltages and currents, for example the tube voltage U. In order to be able to set the latter to the respectively requisite values, the generator unit 17 is assigned a control unit 18 with a keyboard 19, which permits the values to be set as required.

In addition, the operation and control of the CT unit apart from this is carried out by way of the control unit 18 and the keyboard 19, which is illustrated by the fact that the control unit 18 is connected to the image computer 11.

Amongst other things, the number N of the active rows of detector elements 4, and therefore the position of the radiation apertures 3 and 6, can be set. For this purpose, the control unit 18 is connected to the adjustment units 20 and 21 assigned to the radiation apertures 3 and 6. In addition, the rotation time $\tau$ can be set, which is the time needed by the rotary frame 7 for a complete revolution and which is illustrated by the fact that the drive unit 22 associated with the rotary frame 7 is connected to the control unit 18.

The CT images are calculated according to the method described in more detail below.

Figure 3:
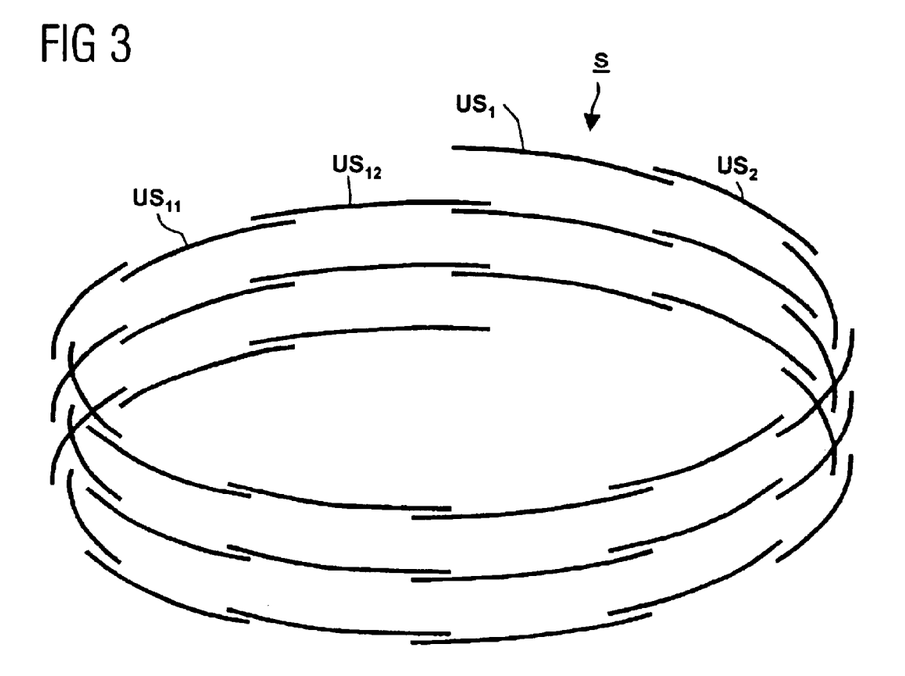
FIG. 3 shows a schematic illustration of a spiral scan with segments and subsegments.

For this purpose, spiral scanning is carried out over $6\pi$, as illustrated, for example, in FIG. 3. Measured data corresponding to a number of mutually overlapping subsegments are extracted from the measured data thereby obtained. In the process, the number and length, for example $\pi/4$ or $\pi/8$, of the subsegments are selected such that these subsegments yield overall at least one spiral segment whose length, for example $\pi+\phi$, suffices to reconstruct a CT image. For each of the subsegments, the corresponding measured data are used to calculate a number of $N_{tilt}$ segment images, whose pixels relate to different image planes inclined with reference to the central plane.

It may be seen from FIG. 3 that, in the case of the exemplary embodiment described, there are twelve mutually overlapping subsegments per full revolution, that is to say it holds that $N_\alpha=12$. The subsegments of the first of the three full revolutions shown in FIG. 3 are designated there by $US_1$ to $US_{12}$.

Figure 4:
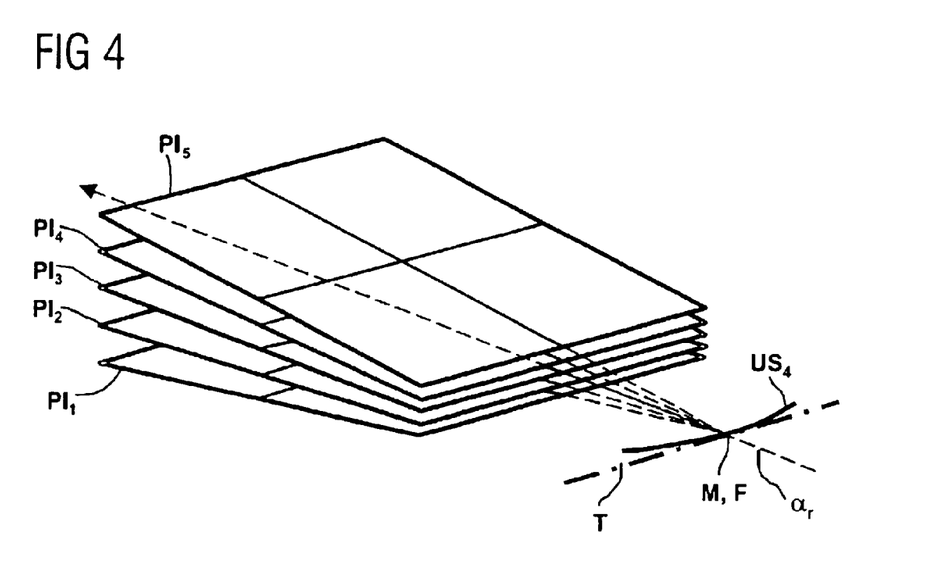
FIG. 4 shows image planes of the segment images belonging to a subsegment.

As may be seen from FIG. 4, using the example of the subsegment $US_4$, five segment images are calculated per subsegment in the case of the exemplary embodiment described, that is to say it holds that $N_{tilt}=5$, which is illustrated by the image planes $PI_1$ to $PI_5$ of the segment images.

Thus, for a full revolution, a total of $N_\alpha * N_{tilt}=60$ segment images are calculated from the measured data of the full revolution, the segment images belonging to a subsegment being combined later to form a component image.

The image planes $PI_1$ to $PI_5$ of the segment images all intersect in a straight line in accordance with FIG. 4. In the case of the exemplary embodiment illustrated, this straight line is the tangent T at the center M of the respective subsegment, that is to say at that point of the segment, belonging to the subsegment, of the focal path that is situated at half the arc length of this segment of the focal path.

For each of these image planes $PI_1$ to $PI_5$, those measured values that correspond to the line integrals required for a reconstruction of the respective segment image are now selected from the measured data supplied from the various detector rows $L_1$ to $L_8$. The selection is performed in such a way that the rays used for the reconstruction of the respective segment image fulfill a suitable error criterion with regard to their distance from the inclined image plane of the respective segment image. This is, in the case of the exemplary embodiment described, the minimum quadratic mean value of the distance, measured in the z direction, of all the rays, used for the reconstruction of the respective segment image, from the respective inclined image plane $PI_1$ to $PI_5$.

The maximum inclination of an image plane of a segment image is therefore determined by the requirement that there must be available, for all the requisite line integrals, measured values whose rays are situated satisfactorily close to the inclined image plane in accordance with the error criterion.

These line integrals assembled from various measured values for each image plane $PI_1$ to $PI_5$ are now used to calculate a segment image belonging to the respective image plane $PI_1$ to $PI_5$, for example by way of the standard reconstruction method of convolution and back projection. The pixels of this segment image belong to the respective inclined image plane $PI_1$ to $PI_5$. Thus, a stack of five segment images is calculated for each subsegment in the case of the exemplary embodiment described.

The $N_{tilt}$ segment images thus obtained per subsegment are combined in a subsequent reformatting step to form component images with reference to a desired target image plane IP that differs from the image planes $PI_1$ to $PI_5$ and cuts the system axis Z at right angles, preferably as illustrated in FIG. 2, specifically as a function of selectable submodes yet to be explained, either by weighting or by interpolation. Independently of the respective submode, the image noise is reduced in the course of the combination, and the desired reconstruction layer thickness is set, the setting being performed by the weighting and/or the number of segment images incorporated into the reformatting, which is, however, preferably equal to the number of segment images reconstructed per subsegment.

The $N_\alpha$ component images thus obtained are combined in a final reformatting step to form a resulting CT image with reference to the target image plane, specifically by addition.

The combination of segment images to form a component image is performed in a first submode by weighting, the procedure in the case of the combination by weighting, which is performed according to one of two selectable weighting modes, independently of the respectively selected weighting mode being such that the pixels of the segment images may in each case contribute as source pixels to a corresponding target pixel of the resulting CT image. Further, the contribution of a source pixel to a target pixel is weighted as a function of a geometric reference variable. The CT number belonging to a target pixel is therefore respectively determined from the CT numbers of the corresponding source pixels taking account of the geometric reference variable.

In the first weighting mode, the distance of the respective source pixel from the corresponding target pixel is taken into account as a geometric reference variable.

In the second weighting mode, in order to avoid artifacts an additional weighting is performed as a function of the distance of the source pixels from the center of the respective subsegment.

In a second submode, the combination of the segment images to form a component image is performed by interpolation, that is to say the target pixels, i.e. the pixels of the resulting CT image, are determined by interpolation, for example linear interpolation, from the corresponding source pixels, that is to say from the corresponding pixels of the segment images.

The conditions forming the basis of the reconstruction of segment images are explained below by way of example with the aid of a subsegment that is centered with reference to a reference projection angle $\alpha_r=0$. Since the image planes of the $n_{ima}$ segment images are inclined both with reference to the x axis by the angle of inclination $\gamma$ and with reference to the y axis by the tilt angle $\delta$, the normal vector of an image plane is given by:

$$\vec{n}(\gamma, \delta) = \begin{pmatrix} \sin\delta \\ -\cos\delta \sin\gamma \\ \cos\delta \cos\gamma \end{pmatrix} \tag{1}$$

The distance $d(\alpha,\delta,\gamma)$ of an arbitrary point $(x_f, y_f, z_f)$ on the spiral path or the considered subsegment in the z direction from the image plane inclined by the angle of inclination $\gamma$ and the tilt angle $\delta$ is given by $$d(\alpha, \delta, \gamma) = \vec{n}(\gamma, \delta) \cdot \begin{pmatrix} x_f + R_f \\ y_f \\ z_f \end{pmatrix} = \vec{n}(\gamma, \delta) \cdot \begin{pmatrix} -R_f \cos\alpha + R_f \\ -R_f \sin\alpha \\ Sp\frac{\alpha}{2\pi} \end{pmatrix} = \tag{2}$$

$$R_f(1 - \cos\alpha)\sin\delta + R_f \sin\alpha\cos\delta\sin\gamma + Sp\frac{\alpha}{2\pi}\cos\delta\sin\gamma.$$

It is assumed in this case that the position $(-R_f, 0, 0)$ of the focus F for the reference projection angle $\alpha_r=0$ lies in the image plane.

The angle of inclination $\gamma$ and the tilt angle $\delta$ of the inclined image plane must be selected in such a way that all the points of the respective subsegment satisfy an error criterion, for example that the quadratic mean value of the distances, measured in the z direction, of all the points of the spiral segment from the image plane is respectively a minimum.

Assuming that b-t is the x-y coordinate system rotated by an angle $\alpha-\pi/2$, b-t is the local coordinate system for a projection with the projection angle $\alpha$.

$x=b \sin\alpha + t \cos\alpha$ $y=-b \cos\alpha + t \sin\alpha \tag{3}$

If a virtual detector array is introduced that corresponds to the projection of the detector array in a plane, the so-called virtual detector plane, containing the system axis z, it holds for the detector plane that t=0.

Each point (x,y,z) on the image plane is designated by $$\vec{n}(\gamma, \delta) \cdot \begin{pmatrix} x + R_f \\ y \\ z \end{pmatrix} = (x + R_f)\sin\delta - y\cos\delta\sin\gamma + z\cos\delta\cos\gamma = 0. \tag{4}$$

Substituting (3) with t=0 in (4) produces the line of intersection of the virtual detector plane with the image plane as follows $$z(b) = -R_f \frac{\tan\delta}{\cos\gamma} - b\left(\sin\alpha\frac{\tan\delta}{\cos\gamma} + \cos\alpha\tan\gamma\right). \tag{5}$$

The z coordinate on the virtual detector plane is given by $$z_{Det}(b) = \tag{6}$$

$$z(b) - Sp\frac{\alpha}{2\pi} = -R_f \frac{\tan\delta}{\cos\gamma} - Sp\frac{\alpha}{2\pi} - b\left(\sin\alpha\frac{\tan\delta}{\cos\gamma} + \cos\alpha\tan\gamma\right).$$

The angle of inclination $\gamma$ is firstly optimized in the same way as in the case of U.S. Pat. No. 5,802,134, that is to say for the tilt angle $\delta=0$. The result is obtained as $$\tan\gamma_0 = \frac{-Sp\,\hat{\alpha}}{2\pi R_f \sin\hat{\alpha}}, \tag{7}$$

$\hat{\alpha}$ being the angle at which the subsegment pierces the image plane.

The tilt angle $\delta$ is optimized for the angle of inclination $\gamma_0$ obtained from (7), with $\hat{\alpha}$. In this case, the optimization criterion for the tilt angle $\delta$ is that the z coordinate in accordance with (6) for the lines $-RFOV \leq b \leq RFOV$ that bound the region, covered by the radiation, of the object to be examined in the z direction at the rear and the front must lie not only within the active detector surface, that is to say within the region of the detector array 5 that is exposed by the radiation aperture 6 and struck by the radiation, but must also utilize the detector surface as effectively as possible.

For the maximum possible tilt angle $\pm\delta_{max}$, the lines, given for the z coordinate in accordance with (6), for $b=\pm RFOV$ reach the end, at the front or rear in the z direction, of the detector surface. When this occurs for the respective subsegment for the projections at the start and end of the subsegment, that is to say for the outermost projection angles $\pm\alpha_1$, it holds that:

$$z_{Det}(b = \pm RFOV) = \pm \frac{SM}{2}, \tag{8}$$

M being the number of detector rows and S being the width of a detector row measured in the z direction.

The result of substituting (5) for $\alpha=\alpha_1$ and $\gamma=\gamma_0$ in (7) and solving for $\delta_{max}$ is:

$$\tan \delta_{max} = \frac{-\frac{SM}{2} + Sp\frac{\alpha_l}{2\pi} \pm RFOV \cos \alpha_l \tan \gamma_0}{-\frac{R_f}{\cos \gamma_0} - (\pm RFOV)\frac{\sin \alpha_l}{\cos \gamma_0}} \quad (9)$$

or $$\pm \delta_{max} = \arctan\left(\frac{-\frac{SM}{2} + Sp\frac{\alpha_l}{2\pi} \pm RFOV \cos \alpha_l \tan \gamma_0}{-\frac{R_f}{\cos \gamma_0} - (\pm RFOV)\frac{\sin \alpha_l}{\cos \gamma_0}}\right)$$

A new $\gamma_{min}$ is determined for the corresponding $\delta_{max}$ by reiteration, specifically by minimizing the quadratic mean value of the distances $d(\alpha, \delta_{max}, \gamma)$, measured in the z direction of all the points of the subsegment from the image plane in accordance with (2).

The range $[-\delta_{max}, \delta_{max}]$ of the tilt angle that is available is now uniformly subdivided in accordance with the number $n_{ima}$ of segment images to be reconstructed, preferably as in the case of the exemplary embodiment described. That is to say, in the case of a uniform subdivision, each image plane $0 \leq i \leq n_{ima}-1$ is designated by the angle of inclination $\gamma_{min}$ (which is preferably equal for all image planes as in the case of the exemplary embodiment described) and the respective tilt angle $\delta_{(i)}$, it holding for the respective tilt angle that $$\delta(i) = \delta_{max} \frac{2i - (n_{ima} - 1)}{n_{ima} - 1}. \quad (10)$$

The reformatting is performed with the aid of interpolation functions of selectable width, as a result of which it is possible to influence the layer sensitivity profile and the image noise in the resulting transaxial tomographic image.

It is advantageous in this case that the desired reconstruction layer thickness of the component images, and thus of the resulting CT images, is established retrospectively in the course of the reformatting.

As a consequence of the circumstance that the reconstruction layer thickness of the desired component tomographic image is established retrospectively, the reconstruction of the segment images is preferably performed by selecting a correspondingly narrow weighting function with the smallest possible reconstruction layer thickness. This ensures the highest sharpness in the z direction not only of the segment images, but also of the component images obtained by the reformatting, as well as of the CT image that has been obtained by the component images.

In addition to this advantage, the following may be named as further advantages of the reformatting described:

- the reconstruction layer thickness can be selected retrospectively without the need for renewed reconstruction,
- the reconstruction layer thickness can be freely selected, and
- a multiplicity of suitable interpolation functions of freely selectable width are available for the reformatting.

Figure 5:
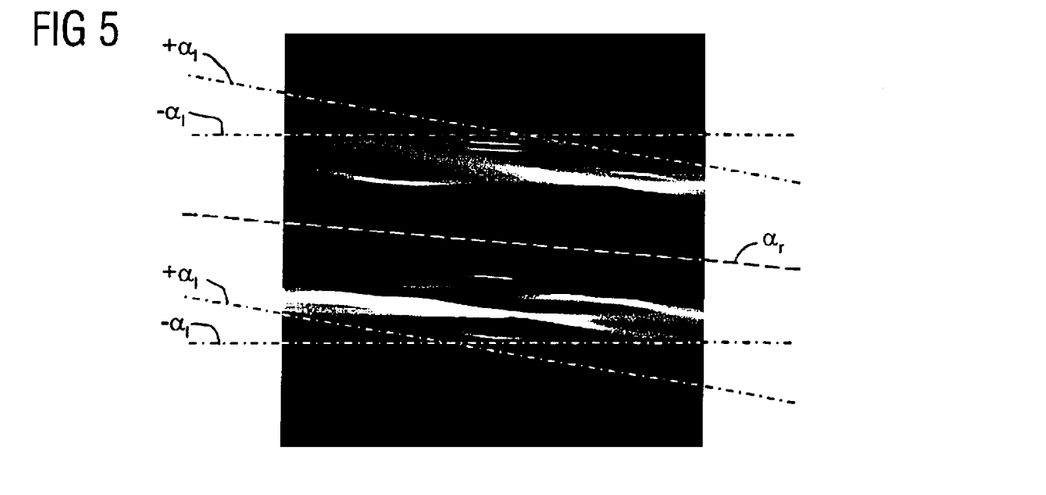
FIG. 5 shows an example of a segment image.

Of the segment images belonging to the subsegment $US_4$, the segment image belonging to the image plane $PI_3$ is illustrated by way of example in FIG. 5. In this case, the reference projection angle $\alpha_r$ and the outermost projection angles $+\alpha_1$ and $-\alpha_1$ belonging to said reference projection angle are indicated by dashes. It emerges that information density in the segment images orthogonal to the projection direction which corresponds to the respective reference projection angle and is designated below as the reference projection direction, is substantially greater than in the respective reference projection direction.

It is therefore possible to compress the data corresponding to the segment images. In the case of the exemplary embodiment described, this is performed as a consequence of the circumstance that, in the case of the use of a homogeneous pixel matrix, the data redundancy owing to said reasons would be very high, the data compression by virtue of the fact that the compressed data corresponding to the segment images have in accordance with the data structure a pixel matrix that is inhomogeneous in such a way that the resolution $R_r$ in the reference projection direction is lower than the resolution $R_{or}$ orthogonal to the reference projection direction. Assuming a given resolution orthogonal to the reference projection direction, the compression factor that can be achieved in the compression corresponds to the quotient $R_{or}/R_r$.

Figure 6:
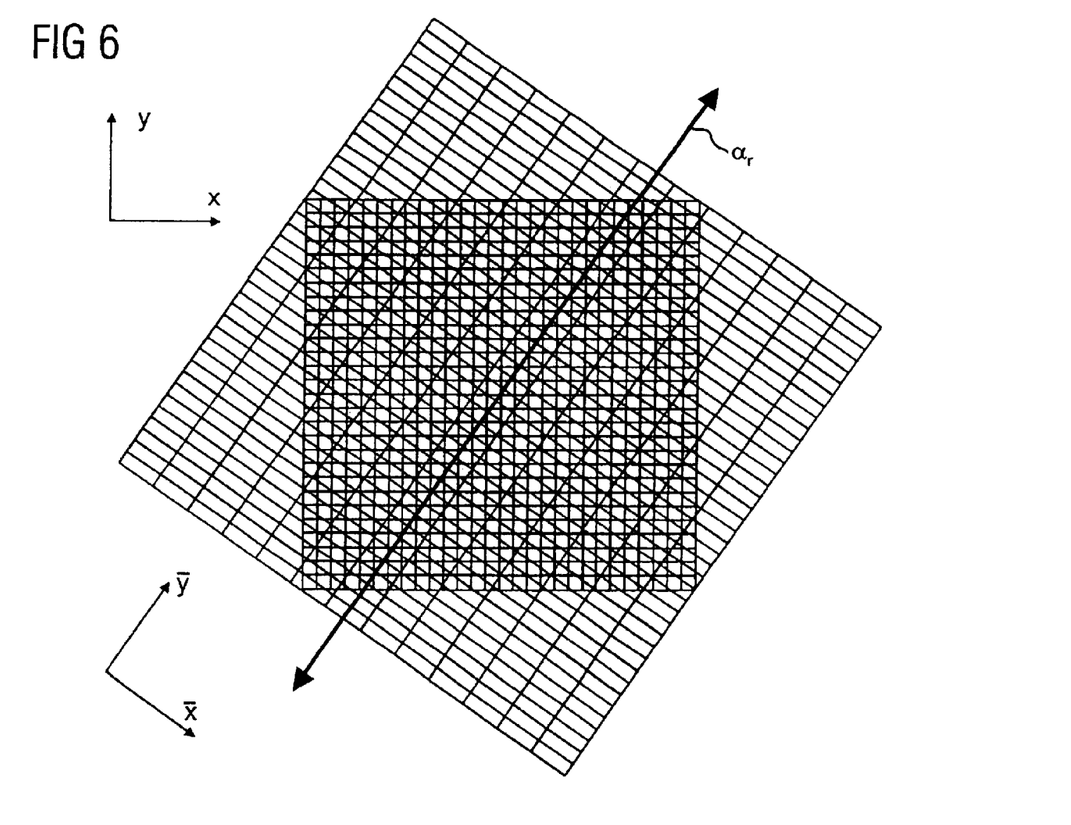
FIG. 6 shows an inhomogeneous pixel matrix of a segment image, and the homogeneous pixel matrix of the associated component image.

In the case of the described exemplary embodiment, the inhomogeneous pixel matrix in accordance with FIG. 6 is implemented by virtue of the fact that the compressed data corresponding to the segment images have pixels of elongated, specifically rectangular shape, the longest extent of the pixels running in the reference projection direction.

When the aim in essence is to reduce the storage space required for storing the segment images, a first compression operating mode is selected for which the segment images are converted to the inhomogeneous pixel matrix after reconstruction has been performed.

If the aim is also to reduce the required computational outlay for reconstructing the segment images, a second compression operating mode is selected in which the procedure is such that the segment images are reconstructed as early as in the inhomogeneous pixel matrix. This offers the advantage that substantially fewer pixels need to be reconstructed than in the case of a homogeneous pixel matrix that has the same resolution orthogonal to the reference projection direction as does the inhomogeneous pixel matrix.

In the course of the reconstruction in the inhomogeneous pixel matrix, the coordinate system, on which the back projection is based, with the $\overline{x}$ and $\overline{y}$ axes is rotated—in accordance with FIG. 5—in each case such that the direction of back projection corresponds to the respective reference projection direction.

Irrespective of which of the two compression operating modes is selected, the data compression must be canceled again at the latest in the course of the combination of the component images to form a resulting CT image. Consequently, it is provided in the case of the CT unit according to an embodiment of the invention that the component images are also produced on the basis of the inhomogeneous pixel matrix, and transition to a homogeneous pixel matrix is not performed until during the course of the production of the resulting CT image. By contrast with the procedure, likewise possible in principle, of already transferring to the homogeneous pixel matrix when combining the segment images belonging to a subsegment to form a component image, this offers the advantage of a reduced storage requirement and a likewise reduced computational outlay.

Irrespective of whether the decompression is performed in the course of combining segment images to form a component image, or of combining component images to form a resulting CT image, when selecting a first operating submode, the pixels of the homogeneous pixel matrix are obtained by interpolation for the pixels of the homogeneous pixel matrix. When selecting a second operating submode, the pixels of the homogeneous pixel matrix are obtained by weighting from the pixels of the inhomogeneous pixel matrix.

In both operating submodes, because of the alignment of the inhomogeneous pixel matrix in accordance with the reference projection direction, the inhomogeneous pixel matrix must be larger than the homogeneous pixel matrix in order, despite the rotation of the inhomogeneous pixel matrix relative to the homogeneous pixel matrix, to ensure that the inhomogeneous pixel matrix contains data suitable for determining each pixel of the homogeneous pixel matrix. In the case of a quadratic homogeneous pixel matrix and a likewise quadratic inhomogeneous pixel matrix, this indicates that (for any desired reference projection direction) the side length of the inhomogeneous pixel matrix must be greater by a factor than that of the homogeneous pixel matrix.

As to the procedure for decompressing the data by interpolation or weighting, what was said above in connection with the combination of a plurality of segment images to form a component image applies mutatis mutandis. The averaging can thus also be performed in a weighted fashion.

In the case of the exemplary embodiments described, the data compression is performed on the basis of the use of an inhomogeneous pixel matrix. Alternatively, other compression methods customary in the field of image processing can be applied.

In the above discussions, there was as yet no account taken of the fact that, when they are obtained from a moving object to be examined, the determined data and segment images have, in part, instances of unsharpness that are caused by different movement states of the object to be examined. In accordance with the idea of an embodiment of the invention, however, the aim is to eliminate this unsharpness of movement by laying over the segment images a weighting that is referred to the movement phase, or, in other words, in order to display the object to be examined, by using only segment images that display the object to be examined in a specific movement state. For example, with reference to the movement of a heart, it is possible to use a relatively long-term phase in which the heart exhibits no movement or only a very slight one.

Figure 7:
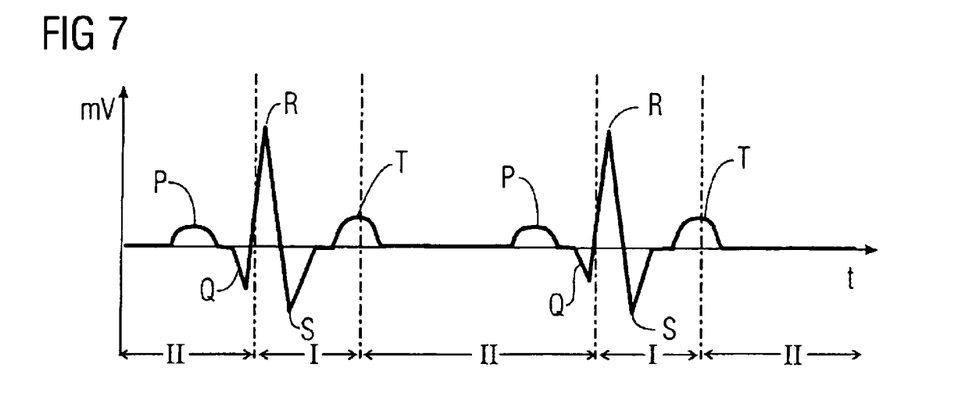
FIG. 7 shows a typical ECG of a human heart.
Figure 8:
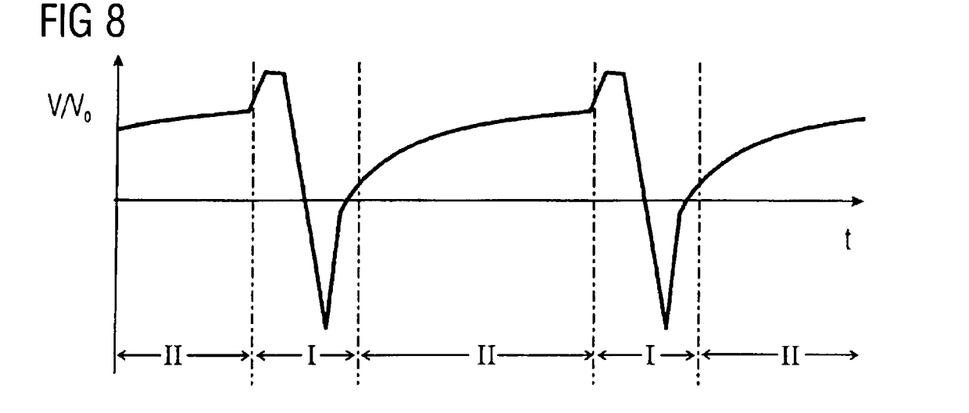
FIG. 8 shows the state of movement of the heart, illustrated by a relative change in volume correlated with the ECG from FIG. 7.
Figure 9:
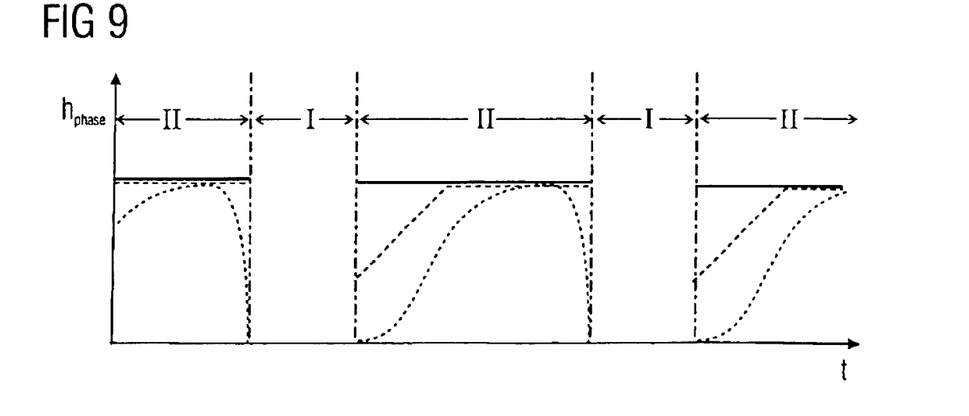
FIG. 9 shows the time profile of the weighting function $h_{phase}$, correlated with FIGS. 4 and 5.

FIGS. 7 to 9 show the temporal correlation between a schematically illustrated ECG picture of a patient.

FIG. 7 shows the generally known typical profile over the atrial deflections with a P wave and P–Q segment, followed by the ventricular deflections with the QRS complex, ST segment, T wave and U wave. Only the P wave, QRS complex and the T wave are emphasized in this illustration as characteristic.

This typical and periodic profile of the ECG is correlated with specific movement states of the heart that are illustrated in FIG. 8, synchronized in time, by a drawing of the relative change in volume $V/V_0(t)$ of the heart. If this profile is divided roughly into two phases, the result is a movement phase I and a rest phase II. According to the invention, the CT pictures each correspond to a specific phase such that the weighting function $h_{phase}$, whose profile is illustrated in FIG. 6, ensures in accordance with the respective phases that only information of this specific movement situation is finally used for imaging.

Since it is possible to assume over a relatively large time period, specifically the rest phase II of the heart, that only slight movement takes place, it may be seen from FIG. 9 that, for example, the entire rest phase II can be heavily weighted, while the movement phase I is lightly weighted. The continuous line in FIG. 9 shows such a profile of the weighting function $h_{phase}$ with only two different values 1 and 0.

Alternatively, however, it is also possible to take account of the actual relative change in volume and thus of the movement state of the heart by introducing different and more finely differentiated weightings depending on the extent to which the heart is resting, as is illustrated in the profile, illustrated by dashes, of the weighting function $h_{phase}$. Moreover, it is also possible to select a weighting function that decreases with distance in time from a predetermined movement state. This is illustrated by way of example by the dotted profile of the weighting function.

Filtering is carried out on the set of segment image planes that bear both a time stamp and a location stamp. The spatio-temporal filter acts on these coordinates. There is a stack (booklet) of segment image planes for each of the segments, the number $N_{tilt}$ being equal for each stack.

According to the invention, a spatio-temporal filter function, by means of which the z resolution and temporal resolution of the target image can be influenced over a wide range, is defined on the set of segment image planes $S(\theta_{R,j}+k\pi, Z_{R,q}(\theta_{R,j}+k\pi))$; where $1 \leq j \leq N_{seg}/2$ (whole numbers k,q).

In this case, $\theta_{R,j}+k\pi$ denotes the central angle of the jth image stack in the kth half revolution ($\theta_{R,j}=\theta_R+(j-1)\cdot\pi/(N_{seg}/2)$), and $$z_{R,q}(\theta_{R,j}+k\pi) = z_{start}(\theta=0) + p \cdot \frac{\theta_{R,j}+k\pi}{2\pi} + (q - N_{tilt}/2) \cdot \Delta z$$

denotes the assigned z positions of the second image planes in the image stack, p being the table feed and $z_{start}$ being the starting position of the spiral revolution at the projection angle $\theta=0$. Otherwise, the segment image planes are functions of the spatial coordinates (x,y) which have initially been omitted for the sake of clarity.

The filtered segment image plane $\hat{S}(\theta_{R,j},z_{img})$ is calculated as follows in relation to the central angle $\theta_{R,j}$ at the z positioning:

$$\hat{S}(\theta_{R,j}, z_{img}) =$$
$$\frac{1}{W_j} \cdot \sum_{k,q} S(\theta_{R,j}+k\pi, z_{R,q}(\theta_{R,j}+k\pi)) \cdot w_z(d(z_{R,q}(\theta_{R,j}+k\pi), z_{img}) \cdot$$
$$w_{phase}(t(\theta_{R,j}+k\pi) - c_R(k)); \text{ where } 1 \leq j \leq N_{seg}/2,$$

$w_z$ being a suitable weighting function that determines the layer thickness, and d denoting the distance for a similar function of the second image plane at the z position $z_{R,q}$ from the z position $z_{img}$.

$$W_j = \sum_{k,q} w_z(d(z_q(\theta_{R,j}+k\pi, z_{img})) \cdot w_{phase}(t(\theta_{R,j}+k\pi) - c_R(k,j))$$

is the weighted sum for correct normalization. The weighting function $w_{phase}$ evaluates the temporal spacing of the segment image planes centered at the angle $\theta_{R,j}+k\pi$ from the temporal position $c_R(k,j)$, determined by means of the ECG, in the cardiac cycle assigned to the angle $\theta_{R,j}+k\pi$.

The CT image at the z position $z_{img}$ is then yielded as:

$$I(x, y, z_{img}) = \frac{1}{N_{seg}/2} \cdot \sum_{j=1}^{N_{seg}/2} \hat{S}(\theta_{R,j}, x, y, z_{img}).$$

In connection with the exemplary embodiments described above, CT units of the third generation are used, that is to say the X-ray source and the detector system are displaced jointly about the system axis during the image production. However, an embodiment of the invention can also be used in conjunction with CT units of the fourth generation, in which only the X-ray source is displaced about the system axis and interacts with a stationary detector ring, if the detector system is a multi-row array of detector elements.

The method according to an embodiment of the invention can also be used in CT units of the fifth generation, that is to say CT units in which the X-radiation does not emanate from only one focus but from a plurality of foci of one or more X-ray sources displaced about the system axis, if the detector system has a multi-row array of detector elements.

The CT units used in conjunction with the exemplary embodiments described above have a detector system with detector elements arranged in the manner of an orthogonal matrix. However, an embodiment of the invention can also be used in conjunction with CT units whose detector system has detector elements arranged in a two-dimensional array in another manner.

Thus, overall, an embodiment of the invention discloses a method for producing CT images of a periodically moving area to be examined, in particular a method for cardio volume reconstruction for multi-row CT units in spiral mode, and a multi-row CT unit designed therefor, a plurality of segment images being calculated per partial revolution segment from small partial revolution segments along a revolution spiral, which segment images are converted in a second step to partial images in the target image plane (for example axial plane) and combined in a third step in the correct phase to form complete images.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for producing CT images of a periodically moving area to be examined, comprising:

scanning the area to be examined with the aid of a beam, emanating from a focus, with a multiplicity of rays relating to a multiplicity of detector elements of a detector array, the focus and the detector array being relatively displaced and supplying data from which a change in attenuation of the rays between the focus and detector elements is determinable;

collecting movement data from the periodically moving area to be examined, the detector data and data resulting therefrom being assignable to the movement states;

using only output data, correlated with a specific movement state of the body region, to compose at least one CT image;

dividing the output data, supplied during the movement of the focus on a spiral segment of sufficient length for reconstructing a CT image and assigned to specific movement states, into output data with reference to $N_{seg}$ subsegments, reconstructing segment images by back projection and filtering, referred to movement state, with an image plane inclined to the system axis;

combining segment images belonging to a subsegment and correlated with a movement state to form a component image, referred to movement state, with reference to a target image plane; and combining component images, referred to movement state, for at least one target image plane to form resulting at least one CT image of a specific movement state.

2. The method as claimed in claim 1, wherein, in order to form the component image from the segment images, a spatio-temporal filter function is applied to the segment images, the spatio-temporal filter function being variable with reference to the spatial resolution in the direction of the system axis and with reference to temporal resolution.

3. The method as claimed in claim 2, wherein the set of segment images is represented by $S(\theta_{R,j}+k\pi, Z_{R,q}(\theta_{R,j}+k\pi))$, wherein $1 \leq j \leq N_{seg}/2$, with k and j representing whole numbers, $\theta_{R,j}+k\pi$ representing the central angle of a jth volume stack in the kth half revolution $\theta_{R,j}=\theta_R+(j-1)\cdot\pi/(N_{seg}/2)$ and $$z_{R,q}(\theta_{R,j}+k\pi) = z_{start}(\theta=0) + p \cdot \frac{\theta_{R,j}+k\pi}{2\pi} + (q - N_{tilt}/2)\cdot \Delta z$$

representing the assigned z positions of the segment images in the volume stack, and wherein p is the table feed and $z_{start}$ is the starting position of the spiral revolution at the projection angle $\theta=0$.

4. The method as claimed in claim 3, wherein the filtered segment images $\hat{S}(\theta_{R,j}, z_{img})$ are calculated in accordance with the rule $$\hat{S}(\theta_{R,j}, z_{img}) = \frac{1}{W_j} \cdot \sum_{k,q} S(\theta_{R,j}+k\pi, z_{R,q}(\theta_{R,j}+k\pi)) \cdot$$
$$w_z(d(z_{R,q}(\theta_{R,j}+k\pi)z_{img}) \cdot w_{phase}(t(\theta_{R,j}+k\pi) - c_R(k)),$$

where $1 \leq j \leq N_{seg}/2$, $w_z$ is a weighting function that determines the layer thickness, and d denotes at least one of the distance and a similar function of the segment image plane at the z position $z_{R,q}$ from the z position $z_{img}$, $w_{phase}$ representing the temporal spacing of the segment image planes centered at the angle $\theta_{R,j}+k\pi$ from the temporal position $c_R(k,j)$, determined relative to the movement state, in the movement cycle, assigned to the angle $\theta_{R,j}+k\pi$, of the object to be examined, and $$W_j = \sum_{k,q} w_z(d(z_q(\theta_{R,j}+k\pi, z_{img})) \cdot w_{phase}(t(\theta_{R,j}+k\pi) - c_R(k,j))$$

corresponding to the weighted sum for correct normalization.

5. The method as claimed in claim 4, wherein the CT image at the z position $z_{img}$ is yielded as:

$$I(x, y, z_{img}) = \frac{1}{N_{seg}/2} \cdot \sum_{j=1}^{N_{seg}/2} \hat{S}(\theta_{R,j}, x, y, z_{img}).$$

6. The method as claimed in claim 1, wherein the segment images are reconstructed for image planes that are inclined with reference to the system axis both by an angle of inclination γ about a first axis cutting the system axis at right angles, and by a tilt angle δ about a second axis cutting both the first axis and the system axis at right angles.

7. The method as claimed in claim 1, wherein neighboring subsegments overlap one another, and wherein the output data belonging to the overlap regions are respectively weighted in such a way that the weights of mutually corresponding output data of the subsegments overlapping one another yield one in each case.

8. The method as claimed in claim 1, wherein segment images for a number $n_{ima}$ of inclined image planes are reconstructed for each subsegment, the image planes having the different z positions $z_{ima}$.

9. The method as claimed in claim 8, wherein the plurality of inclined image planes intersect in a straight line running tangentially to the subsegment.

10. The method as claimed in claim 8, wherein it holds for the extreme values $+\delta_{max}$ and $-\delta_{max}$ of the tilt angle δ inclined image planes belonging to a subsegment that:

$$\pm\delta_{max} = \arctan\left(\frac{-\frac{SM}{2} + Sp\frac{\alpha_l}{2\pi} \pm RFOV\cos\alpha_l\tan\gamma_0}{-\frac{R_f}{\cos\gamma_0} - (\pm RFOV)\frac{\sin\alpha_l}{\cos\gamma_0}}\right)$$

$\gamma_0$ being the value of the angle of inclination $\gamma$ determined for the tilt angle $\delta=0$ in accordance with $$\gamma_0 = \arctan\left(\frac{-Sp\hat{a}}{2\pi R_f \sin\hat{a}}\right).$$

11. The method as claimed in claim 6, wherein, for a given absolute value $|\delta_{max}|$ of the maximum value of the tilt angle $\delta$, the associated optimal value $\gamma_{min}$ of the angle of inclination $\gamma$ is determined in such a way that an error criterion is fulfilled.

12. The method as claimed in claim 6, wherein the tilt angle $\delta$ of the inclined image planes is determined according to $$\delta(i) = \delta_{max}\frac{2i - (n_{ima} - 1)}{n_{ima} - 1}.$$

13. The method as claimed in claim 1, wherein the combination of the plurality of segment images to form a component image is performed by interpolation.

14. The method as claimed in claim 1, wherein the combination of the plurality of segment images to form a component image is performed by averaging.

15. The method as claimed in claim 1, wherein the combination of the plurality of segment images to form a component image is performed by weighted averaging.

16. The method as claimed in claim 1, wherein the combination of the plurality of segment images to form a component image is weighted in accordance with a desired reconstruction layer thickness of the component image.

17. The method as claimed in claim 1, wherein the number of segment images that are combined to produce a component image is selected in accordance with a respectively desired reconstruction layer thickness of the component image.

18. The method as claimed in claim 17, wherein the segment images are reconstructed with the smallest possible layer thickness.

19. The method as claimed in claim 1, wherein the component images are determined for a target image plane that cuts the system axis at right angles.

20. The method as claimed in claim 1, wherein the combination of the component images to form the resulting CT image is performed by adding.

21. The method as claimed in claim 1, wherein the data corresponding to the segment images are compressed.

22. The method as claimed in claim 21, wherein the compressed data corresponding to the segment images have a pixel matrix which is inhomogeneous in such a way that the resolution in a first direction running at least substantially in the direction of the reference projection direction belonging to the respective subsegment is higher than in a second direction which runs at least substantially orthogonal to the reference projection direction.

23. The method as claimed in claim 22, wherein the compressed data to the segment images have pixels of elongated shape, the longest extension of the pixels running at least substantially in the direction of the reference projection direction belonging to the respective subsegment.

24. The method as claimed in claim 23, wherein rectangular pixels are provided.

25. The method as claimed in claim 23, wherein the segment images are converted into the inhomogeneous pixel matrix.

26. The method as claimed in claim 23, wherein the segment images are reconstructed in the inhomogeneous pixel matrix.

27. The method as claimed in claim 26, wherein the back projection direction corresponds at least substantially to the direction of the reference project direction belonging to the respective subsegment.

28. The method as claimed in claim 21, wherein the compression is canceled in the course of the combination of the component images to form a resulting CT image having a homogeneous pixel matrix.

29. The method as claimed in claim 21, wherein the segment images are converted into the inhomogeneous pixel matrix.

30. The method as claimed in claim 21, wherein the pixels of the homogeneous pixel matrix are obtained by interpolation from the pixels of the inhomogeneous pixel matrix.

31. The method as claimed in claim 1, wherein the pixels of the homogeneous pixel matrix are obtained by averaging from the pixels of the inhomogeneous pixel matrix.

32. A CT unit for scanning a periodically moving object to be examined, comprising:
    a beam emanating from at least one focus;
    a detector array including a multiplicity of distributed detector elements for detecting the rays of the beam, the at least one focus being moved relative to the object to be examined on at least one focal path, running around the object to be examined, with a detector array situated opposite thereof; and
    functional means for detecting the movement state of the object to be examined, for collecting the detector data, and for filtering and back projection in accordance with the method of claim 1.

33. The CT unit as claimed in claim 32, wherein the functional means are implemented at least partially by at least one of programs and program modules.

34. The CT unit as claimed in claim 32, wherein an ECG is provided for detecting the movement state of the object to be examined.

35. The method as claimed in claim 9, wherein it holds for the extreme values $+\delta_{max}$ and $-\delta_{max}$ of the tilt angle $\delta$ inclined image planes belonging to a subsegment that:

$$\pm\delta_{max} = \arctan\left(\frac{-\frac{SM}{2} + Sp\frac{\alpha_l}{2\pi} \pm RFOV\cos\alpha_l\tan\gamma_0}{-\frac{R_f}{\cos\gamma_0} - (\pm RFOV)\frac{\sin\alpha_l}{\cos\gamma_0}}\right)$$

$\gamma_0$ being the value of the angle of inclination $\gamma$ determined for the tilt angle $\delta=0$ in accordance with $$\gamma_0 = \arctan\left(\frac{-Sp\hat{a}}{2\pi R_f \sin\hat{a}}\right).$$

36. The method as claimed in claim 24, wherein the segment images are converted into the inhomogeneous pixel matrix.

37. The method as claimed in claim 24, wherein the segment images are reconstructed in the inhomogeneous pixel matrix.

38. The method as claimed in claim 37, wherein the back projection direction corresponds at least substantially to the direction of the reference project direction belonging to the respective subsegment.

39. The CT unit as claimed in claim 33, wherein an ECG is provided for detecting the movement state of the object to be examined.

40. The method for producing CT images as claimed in claim 1, wherein the periodically moving area to be examined includes a cardiac region of a living being.

41. The method for producing CT images as claimed in claim 1, wherein the focus and the detector array are relatively displaced in a fashion rotating on an equidistant spiral path, including a multiplicity of spiral segments, and parallel to the system axis.

42. The CT unit as claimed in claim 32, wherein the CT unit is for scanning a heart.

43. A method for producing CT images of a periodically moving area to be examined, comprising:

supplying data, from which a change in attenuation of rays between a relatively displaceable focus and detector elements of an array is determinable;

collecting movement data from the periodically moving area to be examined, detector data and collected movement data being assignable to the movement states;

using only output data, correlated with a specific movement state, to compose at least one CT image;

dividing the output data, supplied during the movement of the focus on a spiral segment of sufficient length for reconstructing a CT image and assigned to specific movement states, into output data with reference to $N_{seg}$ subsegments, reconstructing segment images with an image plane;

combining segment images belonging to a subsegment and correlated with a movement state to form a component image with reference to a target image plane; and combining component images, referred to movement state, for at least one target image plane to form resulting at least one CT image of a specific movement state.

44. The method as claimed in claim 43, wherein, in order to form the component image from the segment images, a spatio-temporal filter function is applied to the segment images, the spatio-temporal filter function being variable with reference to the spatial resolution in the direction of the system axis and with reference to temporal resolution.

* * * * *